United States Patent
Pang et al.

(10) Patent No.: US 11,340,201 B2
(45) Date of Patent: May 24, 2022

(54) CLOUD-PLATFORM BASED AUTOMATIC IDENTIFICATION SYSTEM AND METHOD OF SEVEN TYPES OF MASS SPECTRUMS FOR PESTICIDES AND CHEMICAL POLLUTANTS COMMONLY USED IN THE WORLD

(71) Applicants: CHINESE ACADEMY OF INSPECTION AND QUARANTINE, Beijing (CN); BEIJING UNI-STAR INSPECTION TECHNOLOGY CO., LTD., Beijing (CN)

(72) Inventors: Guofang Pang, Beijing (CN); Qiaoying Chang, Beijing (CN); Chunlin Fan, Beijing (CN); Hui Chen, Beijing (CN); Xingqiang Wu, Beijing (CN); Ruobin Bai, Beijing (CN); Zijuan Zhang, Beijing (CN)

(73) Assignees: CHINESE ACADEMY OF INSPECTION AND QUARANTINE; BEIJING UNI-STAR INSPECTION TECHNOLOGY CO., LTD.

(*) Notice: Subject to any disclaimer, the term of this patent is extended or adjusted under 35 U.S.C. 154(b) by 0 days.

(21) Appl. No.: 16/475,348

(22) PCT Filed: May 6, 2019

(86) PCT No.: PCT/CN2019/085612
§ 371 (c)(1),
(2) Date: Jul. 1, 2019

(87) PCT Pub. No.: WO2020/191857
PCT Pub. Date: Oct. 1, 2020

(65) Prior Publication Data
US 2022/0050092 A1  Feb. 17, 2022

(30) Foreign Application Priority Data

Mar. 26, 2019 (CN) .......................... 201910234026.5

(51) Int. Cl.
*G01N 30/00* (2006.01)
*G01N 30/86* (2006.01)
(Continued)

(52) U.S. Cl.
CPC ......... *G01N 30/8675* (2013.01); *G01N 27/62* (2013.01); *G01N 30/72* (2013.01);
(Continued)

(58) Field of Classification Search
CPC .... G01N 30/8675; G01N 27/62; G01N 30/72; G01N 30/8624; G01N 2030/8648; G06N 3/08
(Continued)

(56) References Cited

U.S. PATENT DOCUMENTS

2021/0120731 A1* 4/2021 Mota Manhaes .... A01B 79/005

FOREIGN PATENT DOCUMENTS

| CN | 101855700 | 10/2010 | ............... H01J 49/10 |
| CN | 108414610 | 8/2018 | ............. G01N 27/62 |

(Continued)

OTHER PUBLICATIONS

Pang et al., High Resolution Mass Spectrometry—Internet—Data Science Construction of ternary fusion technology Pesticide residue detection technology platform (w/machine translation), Technology and Society, S & T and Society, 2017, vol. 32 No. 12 (41 pgs).

*Primary Examiner* — Michael Maskell
(74) *Attorney, Agent, or Firm* — Hayes Soloway P.C.

(57) ABSTRACT

A cloud server platform end is used to construct a mass spectrum species classification model, extract a mass spectrum data feature, and construct a training model of the convolutional neural network; a user platform end is used to upload the mass spectrum, experiment condition and device data, directly screen and identify the type of the mass spectrum based on the mass spectrum species classification model or the mass spectrum information base, automatically compare and identify the species and name of the pesticides (Continued)

based on the neural network model trained by the cloud server platform end, and feedback the comparison result to the user. The disclosure solves the restriction on the purchase of standards for user, the use of the system is not limited by the location, and the pesticide residues could be detected automatically, quickly and accurately.

20 Claims, 12 Drawing Sheets

(51) Int. Cl.
  *G01N 27/62*     (2021.01)
  *G06N 3/08*      (2006.01)
  *G01N 30/72*     (2006.01)
(52) U.S. Cl.
  CPC .......... *G01N 30/8624* (2013.01); *G06N 3/08* (2013.01); *G01N 2030/8648* (2013.01)
(58) Field of Classification Search
  USPC .......... 250/281, 282; 702/22, 24, 27, 28, 30
  See application file for complete search history.

(56) References Cited

FOREIGN PATENT DOCUMENTS

| | | | |
|---|---|---|---|
| JP | 2018141750 | 9/2018 | ............. G01N 27/62 |
| WO | WO2009048739 | 4/2009 | ............. H01J 49/10 |

\* cited by examiner

CLOUD-PLATFORM BASED AUTOMATIC IDENTIFICATION SYSTEM AND METHOD OF SEVEN TYPES OF MASS SPECTRUMS FOR PESTICIDES AND CHEMICAL POLLUTANTS COMMONLY USED IN THE WORLD

TECHNICAL FIELD

The present invention belongs to the field of pesticides detection, relates to a spectrogram automatic comparison and identification system and method for pesticides and chemical pollutants, and particularly to an intelligent mass spectrogram comparison and identification system and method for pesticides and chemical pollutants based on cloud platform.

BACKGROUND ART

The pesticide residue detection technique is an import research content related to food safety. Scientists from all around the world have dedicated to the research of pesticide residue detection technology in food for a long time. Earlier pesticide residue detection is based on gas chromatography (GC), and the number of pesticides was relatively small, usually several or more than a dozen. With the application of gas chromatography-mass spectrometry (GC-MS), dozens of pesticides could be detected. With the application of gas chromatography-tandem mass spectrometry (GC-MS/MS), the detection technique for pesticide residue in food reaches a higher level, and about 200 pesticides could be detected. Meanwhile, liquid chromatography-tandem mass spectrometry (LC-MS/MS) technique has been wildly used due to its advantage in detection of highly polar and thermally instable pesticides over GC-MS and GC-MS/MS. Researchers generally applies both techniques in pesticide residue detection at the same time because they are complementary. Since 2001, mass spectrometry detection techniques related to GC and LC have become the leading technique in pesticide multi-residues detection.

According to report, there are more than 1,000 pesticides commonly used in the world, and the number is still increasing. Faced with so many pesticides with different properties, and various complex sample matrices, the application of low-resolution mass spectrometry for the routine detection of target compounds could not meet the actual needs. The application of high-resolution mass spectrometry could solve the problems encountered in low-resolution mass spectrometry, and the representatives thereof are time-of-flight mass spectrometry (TOF) and orbit ion trap mass spectrometry (Orbitrap). The high-resolution mass spectrometry applied in the present invention includes liquid chromatography-quadrupole-time of flight mass spectrometry (LC-Q-TOFMS), gas chromatography-quadrupole-time of flight mass spectrometry (GC-Q-TOFMS), linear ion trap-electric field cyclotron resonance orbit trap combined mass spectrometry (LC-LTQ-Orbitrap), liquid chromatography-quadrupole-electrostatic field orbit trap mass spectrometry (LC-Q-Orbitrap-MS) and gas chromatography-quadrupole-electrostatic field orbit trap mass spectrometry (GC-Q-Orbitrap-MS), the greatest advantage in pesticide multi-residues detection is to provide enough sensitivity under full scan mode and to collect as much compound information as possible. At the same time, the compounds can be further confirmed.

There are two problems need to be solved for the application of the above mass spectrometry techniques. First, the mass spectrometry information of the reference standard is required during the establishment of the method; second, the confirmation of the detection result requires comparison with the standard mass spectrum, which is especially important for high-resolution mass spectrometry. In the actual work, there are two ways to obtain the standard mass spectrum, either to use the standard to collect by oneself, or to use commercial mass spectrums provided by instrument company, however, both require large amount of manpower, material resources and financial resources, resulting in big limitations. This is also one of the problems that trouble the researchers.

CONTENT OF INVENTION

To solve the above problems, the present invention applies mainstream mass spectrometers (liquid chromatography-tandem mass spectrometry (LC-MS/MS), gas chromatography-tandem mass spectrometry (GC-MS/MS), liquid chromatography-quadrupole-time of flight mass spectrometry (LC-Q-TOFMS), gas chromatography-quadrupole-time of flight mass spectrometry (GC-Q-TOFMS), linear ion trap-electric field cyclotron resonance orbit trap combined mass spectrometry (LTQ-Orbitrap-MS) liquid chromatography-quadrupole-electrostatic field orbit trap mass spectrometry (LC-Q-Orbitrap-MS) and gas chromatography-quadrupole-electrostatic field orbit trap mass spectrometry (GC-Q-Orbitrap-MS)) to create an electronic ID card for each pesticide in the database. Mass spectrum information is acquired by image processing technique, the detected mass spectrum is classified and modeled by applying deep convolutional neural network, and the image model system is arranged in the background cloud server end, the users can login in the system, upload spectrums of detected pesticide residues on the browser end, and use the intelligent comparison system and method to know what pesticide has been detected according to detection data.

The present invention provides a cloud-platform based spectrum comparison and identification system and method for pesticides and chemical pollutants; can achieve accurate and rapid comparison and identification of the pesticides and the chemical pollutants. The system includes a cloud server platform end and a user platform end;

wherein, the cloud server platform end includes:

a spectrum acquisition unit, which is used to acquire mass spectrum;

a spectrum parameter acquisition unit, which is used to acquire the experiment environment, experiment condition, and experiment parameter data corresponding to the mass spectrum;

a spectrum device acquisition unit, which is used to acquire information of the spectrum detection device corresponding to the mass spectrum;

a spectrum pretreatment unit, which is used to longitudinally splice and pretreat the acquired mass spectrum and extract the spectrum features;

a spectrum classification model unit, which is used to acquire the change value of fitting angle at the pixel point where the highest peak inside the mass spectrum is located and construct mass spectrum classification model.

a pesticide species classification model unit, which is used to train the extracted spectrum features, spectrum detection device information and experimental parameter data by neural network model and to obtain the classification model which can identify the species and/or names of pesticides and chemical pollutants;

the user platform end includes:

a spectrum data uploading unit, which is used to upload the mass spectrum, spectrum description data and experiment parameter data to the system for detection;

a spectrum pretreatment unit, which is used to longitudinally splice and pretreat the mass spectrum to be detected and extract the mass spectrum features;

a spectrum species identification unit, which is used to classify the mass spectrum according to the change value of fitting angle at the pixel point where the highest peak inside the mass spectrum is located;

a spectrum identification unit, which is used to input the extracted spectrum features, spectrum description data and experiment parameter data to the pesticide species classification model, to identify the species and/or names of the corresponding pesticides and chemical pollutants, Preferably, the neural network model is a layer-by-layer refinement convolutional neural network model, the design or usage method thereof is: each pretreated spectrum is inputted to the layer-by-layer refinement convolutional neural network model, to train the spectrum classification model. After pretreatment, the size of the mass spectrum inputted to the layer-by-layer refinement convolutional neural network model for training is 1×1×1626×1626, the meaning of each parameter is: one sample is selected at a time in training set to update the weight, the number of channel for input of image (binary image) is 1, the inputted image size (height× width) is 1626×1626.

The first convolutional layer Conv1 uses the convolution kernel with the size of 11×11×1, which represents that after each convolution operation, the convolution kernel moves 4 pixels. The edge complement pixel p is 0, representing that the image edge is not filled. After Conv1 layer operation, the feature image is outputted, which reflects information such as the spectrum edge contour. The Relu activation function is used to map the convoluted result and control the data range. Next, the local response normalization layer LRN1 normalizes the feature data outputted from the convolutional layer Conv1, and creates a competitive mechanism for the activity of the local neurons, such that the values with larger response become relatively larger and other neurons with smaller feedback is suppressed, so as to enhance model generalization ability. After the calculation of this layer, the size of the feature image remains unchanged. Next, pooling layer Pool1 uses the kernel with the size of 3×3×64 to maximally pool the feature image outputted by the LRN1 layer and reduces calculation and parameter number by sampling.

Convolutional layers Conv2-Conv5 respectively perform corresponding convolution operation for the feature image outputted from the previous layer, the convolutional kernel size is reduced layer by layer, respectively 9×9×64, 7×7×128, 5×5×256, 3×3×512, wherein 64, 128, 256 and 512 respectively correspond to the number of convolution kernels used by the convolutional layer. The more the convolutional kernel used, the higher the obtained feature dimension. After the layer-by-layer convolution operation, the lower-layer features are abstracted into higher dimensional and more refined convolution activation features. The step size and the edge complement pixel size in each convolutional layer are shown in FIG. 3. The local response normalization layer LRN2 normalizes the feature data outputted from the convolutional layer Conv2. The pooling layers Pool2-Pool5 respectively use the kernel with the size of 3×3×128, 3×3×256, 3×3×512 and 3×3×512 to maximally pool the feature image outputted by the previous layer.

The fully connected layer Fc6 connects the local features outputted by the Conv5, three fully connected layers, Fc6-Fc8, filter the features which perform well in the classification task by learning all the weights during the training process, and send the features into the Softmax-loss layers. The Dropout layers, Dop6 and Drop7, are used in the calculation results of Fc6 and Fc7 respectively, and randomly disable partial nodes of the hidden layer to speed up the training speed and prevent overfitting. The Softmax-loss layer is like a classifier, and calculates the value of loss function. In the training process, the stochastic gradient descent algorithm is used to update the weight and the initial learning rate is set as 0.0001. By minimizing the loss function, the classification effect is gradually improved, and a layer-by-layer refinement convolutional neural network classification model having better classification effect is obtained.

Preferably, the spectrum includes the mass spectrum and/or chromatographs.

Preferably, the spectrums include one or more of the followings: liquid chromatography-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

Preferably, the mass spectrum classification model unit classifies, according to the change value of angle at the pixel point where the highest peak inside the mass spectrum is located: the change value of fitting angle of the ion chromatogram in liquid chromatography-tandem mass spectrum is in the range of $x_{11}$-$x_{12}$, and the change value of fitting angle of ion mass spectrum under 4 collision energies is in the range of $x_{13}$-$x_{14}$; the change value of fitting angle of the ion chromatogram in liquid chromatography-quadrupole-time of flight mass spectrometry is in the range of $x_{21}$-$x_{22}$, and the value of fitting angle of ion mass spectrum under 4 collision energies is $x_{23}$; the change value of fitting angle of the ion chromatogram in linear ion trap-electric field cyclotron resonance orbit trap combined mass spectrum, is in the range of $x_{31}$-$x_{32}$, the value of fitting angle of full scan mass spectrum under ionization mode is $x_{33}$; the change value of fitting angle of the primary mass spectrum in gas chromatography-tandem mass spectrum is $x_{41}$, the value of fitting angle of ion mass spectrum under 4 collision energies is $x_{43}$; the change value of fitting angle of the ion chromatogram in liquid chromatography-quadrupole-electrostatic field orbit trap mass spectrometry is $x_{51}$, the value of fitting angle of fragment ion mass spectrum is $x_{53}$; the value of fitting angle of the mass spectrum in gas chromatography-quadrupole-time of flight mass spectrum is $x_{61}$; the change value of fitting angle of the total ion chromatogram in gas chromatography-quadrupole-electrostatic field orbit trap mass spectrometry is in the range of $x_{71}$-$x_{72}$, the value of fitting angle of full scan mass spectrum under ionization mode is $x_{73}$. Wherein value range of $x_{11}$-$x_{73}$ is 0°-40°.

Preferably, the mass spectrum classification model unit converts the grayscale image of mass spectrum into binary image and assigns the image values to a two-dimensional matrix; according to the matrix value, the position of the pixel point (the row and column of matrix) where the highest peak of the image (the highest peak of the spectrum) is located is determined. With this point as the center, traversal is performed to the lower-left and lower-right area to obtain the row and column of a matrix with the corresponding matrix value of 1, and the image angle of the highest peak after fitting is recorded and stored.

Preferably, the change value of angle at the pixel point, where the highest peak inside the mass spectrum is located, is calculated according to the gradient vector. Around a straight line or a curve, the gradient vector is perpendicular to the straight line or the curve, the angle could be calculated by the orientation change of gradient vector. The gradient vector at a point on the curve is the vertical line of the curve segment passing through the point. A short line segment near the point replaces the curve segment, and the vertical line of the line segment is calculated as the gradient vector. The line segment near the point is determined by the neighborhood chain length, and for different chain length, the calculated gradient vector is slightly different. The orientation of the gradient vector is its angle size.

Preferably, $P_n = \{p_1, \ldots, p_n\}$ is the ordered points set on a curve or a straight line. $L_n = \{l_1, \ldots, l_n\}$ is a short line segment near the ordered points on a curve or a straight line, $l_i$ (i=1, ..., n) represents the line segment with point $p_i$ as the center and having a neighborhood chain length of m (i.e., connecting points $p_{i-m}$ and $p_{i+m}$). In this system, the value of m can be the value between 1 and 5. $S_n = \{s_1, \ldots, s_n\}$ represents the set of slopes of the vertical line of line segment $l_i$. $A_n = \{a_1, \ldots, a_n\}$ represents the set of angle of the vertical line of $l_i$ near point $p_i$, $a_i$ should be in the range of [0, 360°].

the slope of the line segment $l_i$ near the point $p_i(x_i, y_i)$ (connecting the point $p_{i-m}(x_{i-m}, y_{i-m})$ and the point $p_{i+m}(x_{i+m}, y_{i+m})$) is:

$$g_i = (y_{i+m} - y_{i-m})/(x_{i+m} - x_{i-m})$$

the slope of vertical line of line segment $l_i$ is $(-1/g_i)$, i.e.:

$$s_i = (x_{i+m} - x_{i-m})/(y_{i+m} - y_{i-m})$$

the calculation method of $a_i$ is shown in table 2.

TABLE 2

| | No Slope | Slope = 0 | Slope > 0 | Slope < 0 |
|---|---|---|---|---|
| $a_i$ | $a_i = \pi/2$ | $a_i = \pi$ | $a_i = \arctan k_i$ | $a_i = \pi + \arctan k_i$ |

Preferably, the spectrum identification unit screens the mass spectrum data which may be similar to the species of mass spectrum to be detected from the existing mass spectrum database, according to the mass spectrum description data, experiment parameters and number of mass spectrums before inputting the mass spectrum to be detected into the classification model. The Fc7 layer features are extracted from the mass spectrum to be detected, and the cosine similarity between this Fc7 layer feature and the Fc7 layer features of all pretreated mass spectrum selected from the database to find the spectrum with the highest degree of similarity to the current mass spectrum to be detected and determine whether the similarity is higher than 50%. If the similarity is higher than 50%, the mass spectrum inputted by the user is identified successfully.

Preferably, the cosine similarity is calculated as following:

$$\cos\theta = \frac{\sum_1^{dn}(A_i \times B_i)}{\sqrt{\sum_1^{dn} A_i^2} \times \sqrt{\sum_1^{dn} B_i^2}}$$

wherein, $A_i$ represents the ith feature value of spectrum A; $B_i$ represents the ith feature value of spectrum B; $d_n$ represents the total dimension number of the features;

Correspondingly, the present invention also provides a cloud-platform based identification method of seven types of mass spectrum for pesticides and chemical pollutants, including:

to acquire mass spectrum from the cloud server platform end and to acquire the experiment environment, experiment condition and experiment parameter data corresponding to the mass spectrum;

to acquire the detection device information corresponding to the mass spectrum;

to longitudinally splice and pretreat the acquired mass spectrum and to extract the features thereof;

to acquire a change value of fitting angle at a pixel point where the highest peak inside the mass spectrum is located, and to construct a mass spectrum classification model;

to use the neural network model to train the extracted mass spectrum feature, spectrum detection device information and experiment parameter data, and to obtain a pesticide species classification model which can identify the species and/or name of pesticides and chemical pollutants.

to upload the mass spectrum to be detected, mass spectrum description data and experimental parameter data to the system at the user platform end.

to longitudinally splice and pretreat the mass spectrum to be detected, and to extract the features of the mass spectrum;

to classify the mass spectrum according to the change value of fitting angle at the pixel point where the highest peak inside the mass spectrum is located;

to input the extracted spectrum features, mass spectrum description data and experiment parameter data into the pesticide species classification model to identify the species and/or name of corresponding pesticides and chemical pollutants.

The cloud-platform based spectrum comparison and identification method for the pesticides and the chemical pollutants provided in the present invention constructs the spectrum classification model on the cloud server platform end, extracts the spectrum data features and constructs the training model of the convolutional neural network. The user platform end is used for the user to upload the mass spectrum, experiment condition and device data. Based on the mass spectrum classification model of the cloud server platform end, the mass spectrum species are identified. Based on the neural network model obtained by training in the cloud server platform, end, the species and name of pesticides are automatically compared and identified, and the comparison result is fed back to the user. This system solves the restriction on the purchase of standard material for the user, the use of the system is not limited by location, and it can detect the pesticides and the chemical pollutants rapidly and accurately.

The beneficial effects of the present invention:

1. The present invention covers seven types of mainstream chromatography-mass spectrometry techniques, i.e. liquid chromatography-tandem mass spectrometry LC-MS/MS (605 species), gas chromatography-tandem mass spectrometry GC-MS/MS (619 species), liquid chromatography-quadrupole-time of flight mass spectrometry LC-Q-TOFMS (510 species), gas chromatopaphy-quadrupole-time of flight mass spectrometry GC-Q-TOFMS (753 species), linear ion trap-electric field cyclotron resonance orbit trap combined mass spectrometry LC-LTQ-Orbitrap-MS (378 species), liquid chromatography-quadrupole-electrostatic field orbit trap mass spectrometry LC-Q-Orbitrap-MS (570 species) and gas chromatography-quadrupole-electrostatic field orbit trap mass spectrometry OC-Q-Orbitrap-MS (664 species). The unique electronic identity card information of over 1,200 pesticides and chemical pollutants has been established; necessary parameters for chromatography-mass spectrometry analysis and identification, such as the mass spectrum information database (exact mass number, isotope distribution, isotope abundance) and feature spectrum database of mass spectrum (total ion chromatogram and fragment ion mass spectrum under different collision energies). It establishes theoretical and methodological basis for research and development of high-throughput pesticide multi-residues detection techniques. It has technique innovation, and is nowadays the most accurate, sensitive and reliable detection technique. It is the only accurate detection technique which can achieve the largest single-pass pesticide cluster detection.

2. The present invention can realize intelligent matching, comparison and identification, and qualitative identification for mass spectrum of over 1,200 pesticides and chemical pollutants commonly used in the world. Classification search can be performed according to the compound composition, including organohalogen pesticides, organophosphorus pesticides, pyrethroid pesticides, carbamate pesticides, organic nitrogen pesticides, organic sulfur pesticides etc.; according to pesticide function, including insecticides, fungicides, herbicides, acaricides, nematicides, insect growth regulators, plant growth regulators, and persistent environmental pollutants such as polychlorinated biphenyls and polycyclic aromatic hydrocarbons; according to pesticide toxicity, including slight toxic, low toxic, medium toxicity, high toxicity, extreme toxicity, and prohibited pesticides. For the identification of known compounds, comprehensive chromatography-mass spectrum information such as the molecular structure of the compound and fragment ions under different conditions can be quickly obtained by chromatography-mass spectrum atlas. The detection and identification method can be established scientifically, reasonably and quickly, to ensure the accuracy and reliability of the detection and identification results for targets.

3. The present invention can realize the identification of the unknown compounds. The unknown compounds are measured under the assigned chromatography-mass spectrometry condition, to acquire the chromatography-mass spectrum information, such as the exact mass number, total ion chromatogram and secondary fragment ion mass spectrum; through the comparison with the system information, the nature of unknown compound can be rapidly and accurately determined.

4. The present invention can confirm the same compound on different devices, which improves the identification and confirmation ability. The detection of residues of pesticide and chemical pollutant in complex matrices is often interfered by the co-extracted matrix, and false positive result easily occur, and sometimes different types of instruments are needed for confirmation. The present invention comprises chromatographs-mass spectrums of 7 different chromatography-mass spectrometry instruments under different condition, which are complementary to each other, expand the application field, is in line with actual work, and has strong reference.

5. The standard high resolution mass spectrum in the present invention provides basis for confirmation of pesticide multi-residues detection result, there is no need to purchase a large amount of real reference standards for collecting mass spectrums by oneself. Then intelligent and automatic spectrum retrieval and comparison is achieved, the cost of pesticide residues detection is saved, and the ability of market-oriented rapid detection is improved. Meanwhile, it greatly facilitates the detection of the pesticides and chemical pollutants, so that the analysts have a reference basis when establishing methods, and have a query tool when confirming the result. It has important application value and high economic benefit.

6. The present invention realizes the electronization of spectrum data and automation of data retrieval, and develops a relatively complete and globally advanced detection database of pesticide information and pesticide residues with completely independent intellectual property rights in China. It is not only a major contribution to the chromatography-mass spectrometry in the world, but also has great scientific and social significance to the pesticide residue analysis, food safety and environment safety detection, and import-export inspection and quarantine in China.

7. Through the integration, development and utilization of the chromatography-mass spectrum information bases in the present invention, the construction of pesticide residues detection laboratories in China will be rapidly improved, and the overall level and detection efficiency of pesticide identification and pesticide residue detection will be improved, which has high social significance. The construction of retrieval system will greatly improve the data analysis ability of samples and identification ability of pesticides and the screening detection ability of the target pesticides, and has a good application prospect and economic value.

8. The present invention has four major functions: a guidebook for the development of new technique of pesticide residues detection, a reference book for the identification of unknown compound, a textbook for technical training, and a handbook for daily work. These four major functions will play a greater role when the automatic identification system of seven types of chromatography-mass spectrums for the pesticides and chemical pollutants commonly used in the world is established.

EMBODIMENTS

In order to further clarify the objects, technical solutions and advantages of the present invention, the technical solutions of the present invention will be clearly and completely described in the following with reference to the specific examples and corresponding drawings. It is apparent that the described examples are only a part, not all, of the present invention. All other examples, which can be obtained by the person skilled in the art without creative efforts on the basis of the examples of the present invention, are within the scope of the present invention.

Figure 1:
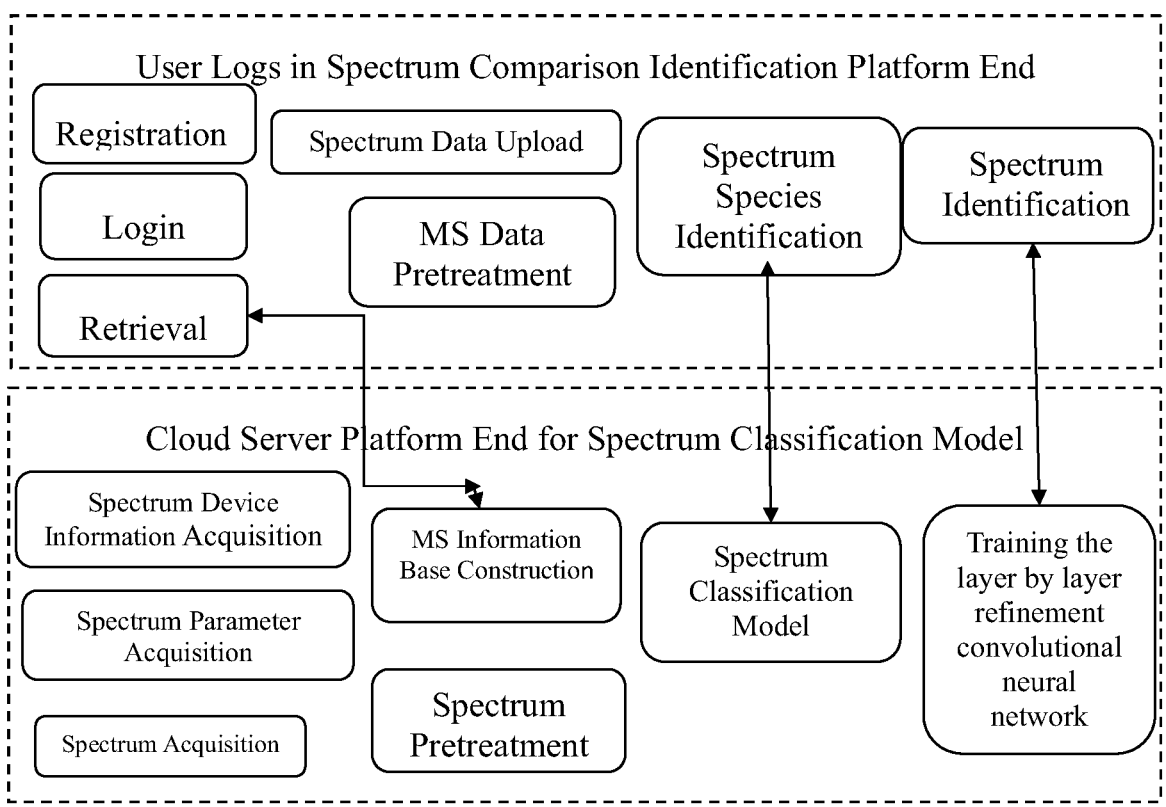
FIG. 1 is a system structural view of the mass spectrum comparison system according to the present invention.

FIG. 1 shows the schematic view of cloud-platform based spectrum comparison system for pesticides and chemical pollutants according to the present invention; this system includes a cloud server platform end and an user platform end, wherein, the user platform end includes an user registration module, an user login module, an user retrieval module, a spectrum data uploading module, a mass spectrum pretreatment module, a mass spectrum specie identification module and a mass spectrum identification module; the cloud server platform end includes a spectrum device information acquisition module, a spectrum parameter acquisition module, a mass spectrum acquisition module, a mass spectrum information base, a mass spectrum pretreatment module, a mass spectrum classification model module and a pesticide species classification module.

At the cloud server platform end, the mass spectrum acquisition module receives the mass spectrum uploaded by the user, the spectrum device information acquisition module receives the spectrum device information uploaded by the user, the spectrum parameter acquisition module receives the information uploaded by the user, such as experiment environment, experiment condition, experiment parameter; wherein, the spectrum uploaded by the user may be mass spectrum or extract ion chromatogram. FIGS. 3-12 show several examples of spectrum that can be processed by the present invention. The person skilled in the art should understand these spectrums are schematic examples of the types of spectrums that can be processed by the spectrum comparison system of the present invention, but spectrums that can be processed by the present invention are not limited thereto.

Preferably, the original spectrums of the present invention include seven types of mass spectrums, including liquid chromatograph-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

The mass spectrum pretreatment module can pretreat the received mass spectrum, to meet the processing requirements, specifically, the mass spectrum pretreatment includes vertical splicing, logarithmic transformation, gamma correction, histogram equalization, and geometric transformation, such as rotation, translation and scaling of the spectrum, and the features of the pretreated mass spectrum will be extracted.

Preferably, the mass spectrum classification model unit classifies, according to the change value of angle at the pixel point where the highest peak inside the mass spectrum is located: the change value of fitting angle of the ion chromatogram in liquid chromatography-tandem mass spectrum is in the range of x11-x12, and the change value of fitting angle of ion mass spectrum under 4 collision energies is in the range of x13-x1.4; the change value of fitting angle of the ion chromatogram in liquid chromatography-quadrupole-time of flight mass spectrometry is in the range of x21-x22, and the value of fitting angle of ion mass spectrum under 4 collision energies is x23; the change value of fitting angle of the ion chromatogram in linear ion trap-electric field cyclotron resonance orbit trap combined mass spectrum, is in the range of x31-x32, the value of fitting angle of full scan mass spectrum under ionization mode is x33; the change value of fitting angle of the primary mass spectrum in gas chromatography-tandem mass spectrum is x41, the value of fitting angle of ion mass spectrum under 4 collision energies is x43; the change value of fitting angle of the ion chromatogram in liquid chromatography-quadrupole-electrostatic field orbit trap mass spectrometry is x51, the value of fitting angle of fragment ion mass spectrum is x53; the value of fitting angle of the mass spectrum in gas chromatography-quadrupole-time of flight mass spectrum is x61; the change value of fitting angle of the total ion chromatogram in gas chromatography-quadrupole-electrostatic field orbit trap mass spectrometry is in the range of x71-x72, the value of fitting angle of full scan mass spectrum under ionization mode is x73. Wherein value range of x11-x73 is 0°-40°.

The mass spectrum classification model unit converts the grayscale image of mass spectrum into binary image and assigns the image values to a two-dimensional matrix; according to the matrix value, the position of the pixel point (the row and column of matrix) where the highest peak of the image (the highest peak of the spectrum) is located is determined. With this point as the center, traversal is performed to the lower-left and lower-right area to obtain the row and column of a matrix with the corresponding matrix value of 1, and the image angle of the highest peak after fitting is recorded and stored.

The pesticide species classification model module performs classification model training for the pesticide species, detection device categories, experiment parameters, mass spectrum features and the pesticides name, etc., to obtain a layer-by-layer refinement convolutional neural network training model, which can be applied to spectrum comparison of pesticides and chemical pollutants and detection of pesticide at the user platform end. The cloud server platform end also includes a mass spectrum information base which stores data such as the spectrum types, the pesticide names, the pesticides species, and the corresponding spectrum, and can be used by the user platform end for search of the corresponding mass spectrum according to the spectrum type and/or the pesticide name and/or the pesticide species.

At the user platform end, the users could register and login the system by the user registration module and the user login module; wherein, the user registration module can provide registration with different authority, for example, the user can register as a user with the authority of uploading information (such as uploading a training sample etc.), or as a user with the only authority of query; the administrator will review the user registration information after user registration, and only after passing the audit, the user can login the system.

After the user successfully registers and logs in the system, the user uses spectrum data upload module to upload the mass spectrum to be detected, spectrum description data and experiment parameter data to the system to obtain the information of detected pesticide; wherein, the spectrum description data include the experiment device information, spectrum species etc.; experiment parameter data include information of experiment environment, experiment condition, experiment parameter etc. Specifically, when upload the mass spectrums to be detected, the user can upload single spectrum or multiple spectrums at the same time, the uploaded spectrum can be of any spectral format commonly used in the art.

After the user uploads the mass spectrum to be detected, the mass spectrum pretreatment module will pretreat the mass spectrum, including vertical splicing, logarithmic transformation, gamma correction, histogram equalization, and geometric transformation, such as rotation, translation and scaling, and the features of the pretreated spectrum will be extracted.

The mass spectrum species identification module inputs the spectrum extracted by mass spectrum pretreatment module into the mass spectrum classification model for matching and identification.

The mass spectrum identification module reads the trained layer-by-layer refinement convolutional neural network model which is stored at the cloud server platform end, and inputs the spectrum features, the spectrum description data and the experiment parameter data, which are extracted by the spectrum pretreatment module into the convolutional neural network model for comparison and identification, to obtain the species and name of pesticide corresponding to the mass spectrum to be detected.

According to another preferable embodiment of the present invention, the spectrum identification unit screens the mass spectrum data which may be similar to the species of mass spectrum to be detected from the existing mass spectrum database, according to the mass spectrum description data, experiment parameters and number of mass spectrums before inputting the mass spectrum to be detected into the classification model, to reduce the number of times of similarity comparison and further reduce the computational complexity of the classification model. Specifically, the Fc7 layer features are extracted from the mass spectrum to be detected, and the cosine similarity between this Fc7 layer feature and the Fc7 layer features of all pretreated mass spectrum selected from the database to find the spectrum with the highest degree of similarity to the current mass spectrum to be detected and determine whether the similarity is higher than 50% If the similarity is higher than 50%, the mass spectrum inputted by the user is identified successfully. Wherein, the cosine similarity is calculated as following:

$$\cos\theta = \frac{\sum_1^{dn}(A_i \times B_i)}{\sqrt{\sum_1^{dn} A_i^2} \times \sqrt{\sum_1^{dn} B_i^2}}$$

wherein, $A_i$ represents the ith feature value of spectrum A; $B_i$ represents the ith feature value of spectrum B; $d_n$ represents the total dimension number of the features.

According to the above cloud-platform-based pesticide and chemical pollutants spectrum comparison system provided in the present invention, the sample data is used to train the layer-by-layer refinement convolutional neural network model at the cloud server platform end, the user platform end receives the mass spectrum and experiment parameter information uploaded by the user, and uses the above neural network model to identify the species and name of the pesticide corresponding to the mass spectrum uploaded by the user. The system can automatically identify the mass spectrum to be detected without manual search and comparison among the large amount of standard spectrums. The species and names of the pesticides and chemical pollutants corresponding to the spectrum to be detected can be obtained quickly, and the efficiency and accuracy of the pesticide residues detection are improved.

Figure 2:
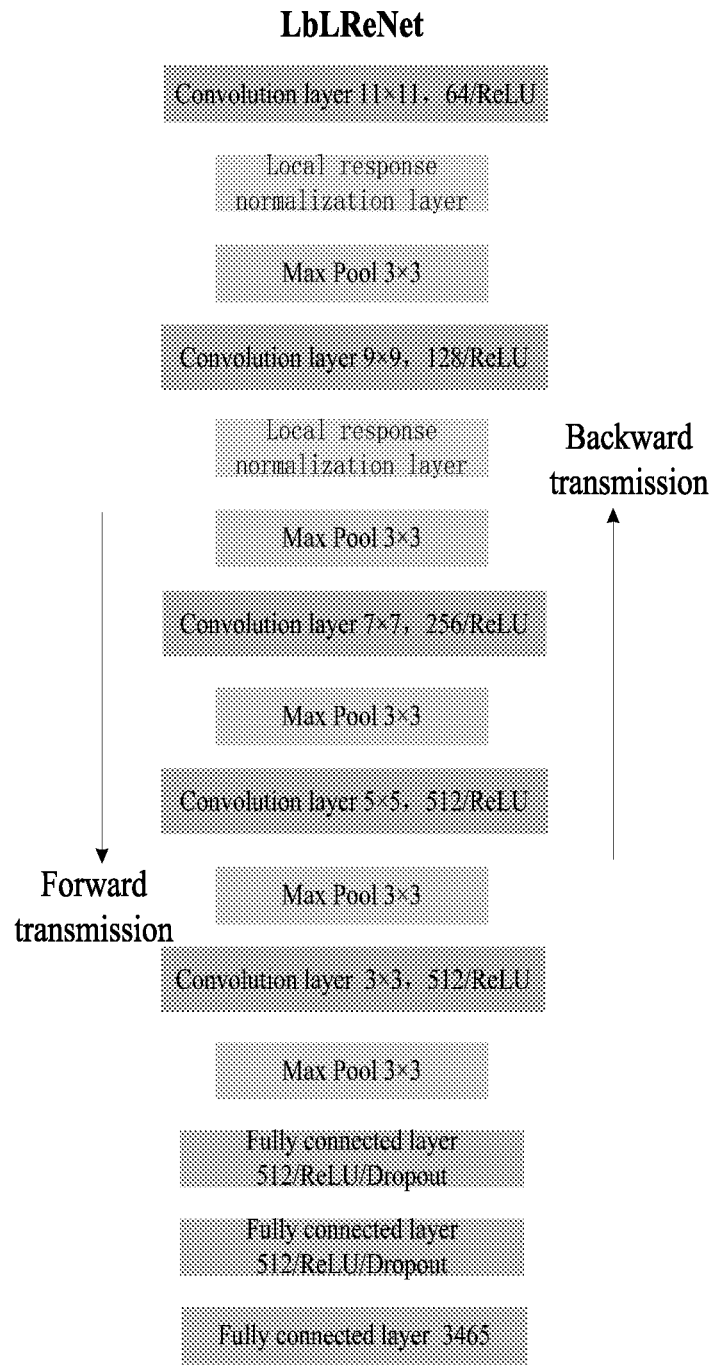
FIG. 2 is a layered structure view of the layer-by-layer refinement convolutional neural network according to the present invention.

FIG. 2 shows the network structure of the Layer-by-Layer Refinement Convolutional Neural Network (Layer-by-Layer Refinement Network, LbLReNet) of the present invention. The mass spectrum and ion mass spectrum of the pesticides are relatively sparse spectrum. For sparse data, when using a relatively small convolutional kernel, the local receptive field is relatively small, and the convolution operation cannot express its characteristics. Large convolutional kernels will lead to a significant increase in complexity. So the present invention designs the convolutional neural network structure of LbLReNet. Specifically, layer-by-layer refinement convolutional neural network structure in the present invention includes five convolutional layers, a ReLU activation function layer, a local response normalization (LRN) layer, a pooling layer and a fully connection layer. Wherein, the lower convolution layer focuses on the contour edge information of the spectrum. As the number of layers increases, the convolution kernel size decreases layer by layer, and the convolutional layer abstracts the lower layer features into higher dimensional and more refined convolution activation features. In addition, the LRN layer normalizes the convolved results. After normalization, the variance of the variables is the same, so it will accelerate the training of the model. The pooling layer reduces the amount of calculation and number of parameter by sampling and changes the dimension of the output. The fully connected (FC) layer connects the previous local features and feeds them to the softmax classifier to train the classifier. Dropout randomly disables a portion of nodes of the hidden layer, speeds up the training and prevents overfitting.

According to the layer-by-layer refinement convolutional neural network structure mentioned in the present invention, a five-layer convolution layer and its corresponding ReLU activation function are designed based on characteristics of the pesticide detection spectrum for the neural network structure, the training speed of the model is accelerated by combining the LRN layer, the pooling layer and the FC layer. The model has the characteristics of rapidly training the model and high accuracy and can be used to identify the species of pesticide residues quickly and accurately.

Figure 3:
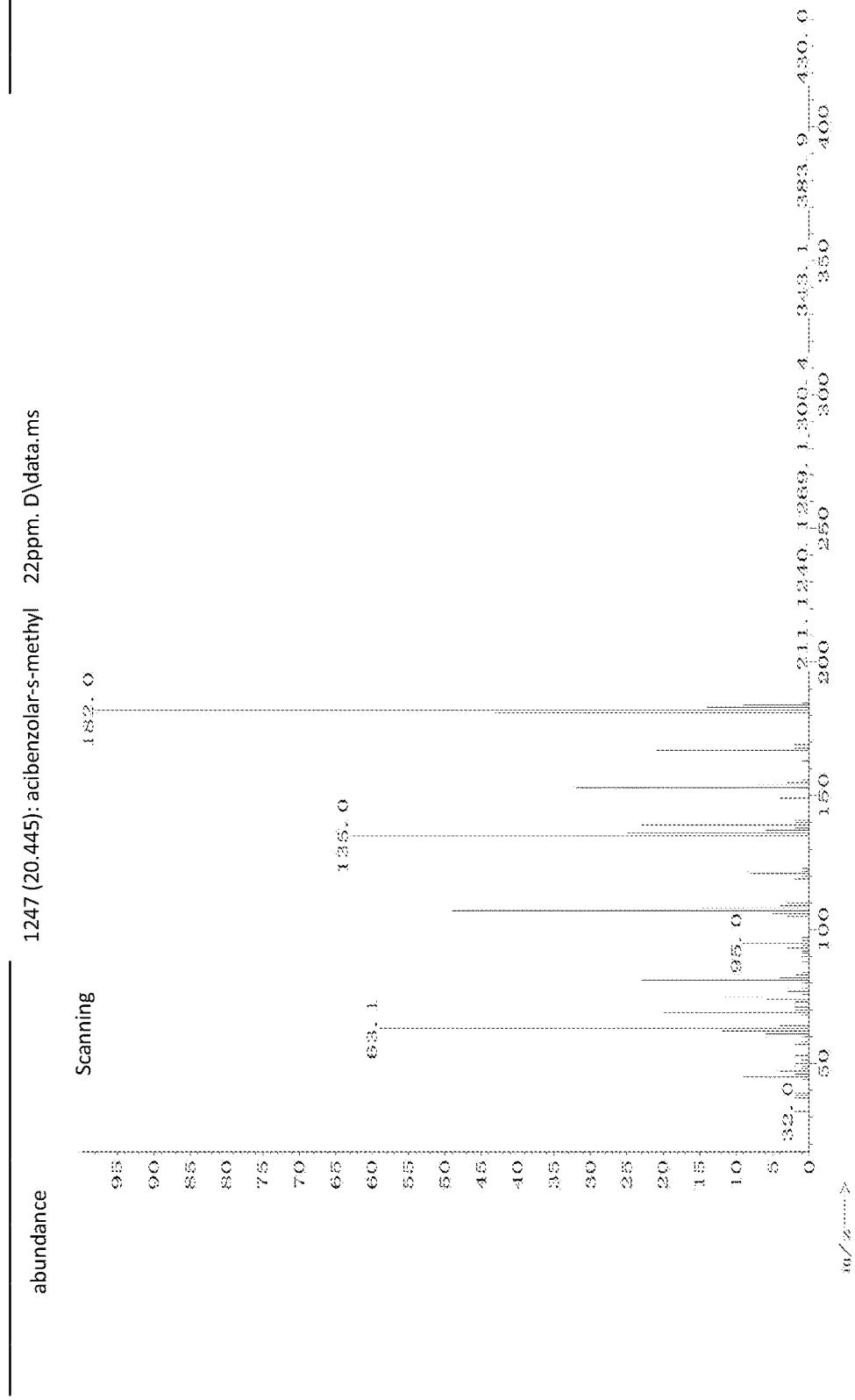
FIG. 3 is a primary mass spectrum according to an example of the present invention
Figure 4:
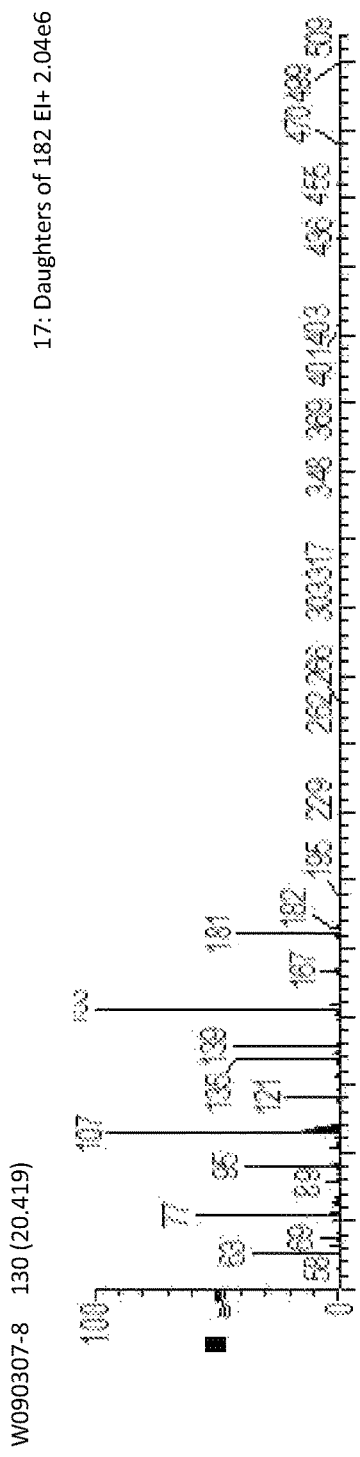
FIG. 4 is a daughter-ion mass spectrum under the corresponding collision energy according to an example of the present invention.
Figure 5:
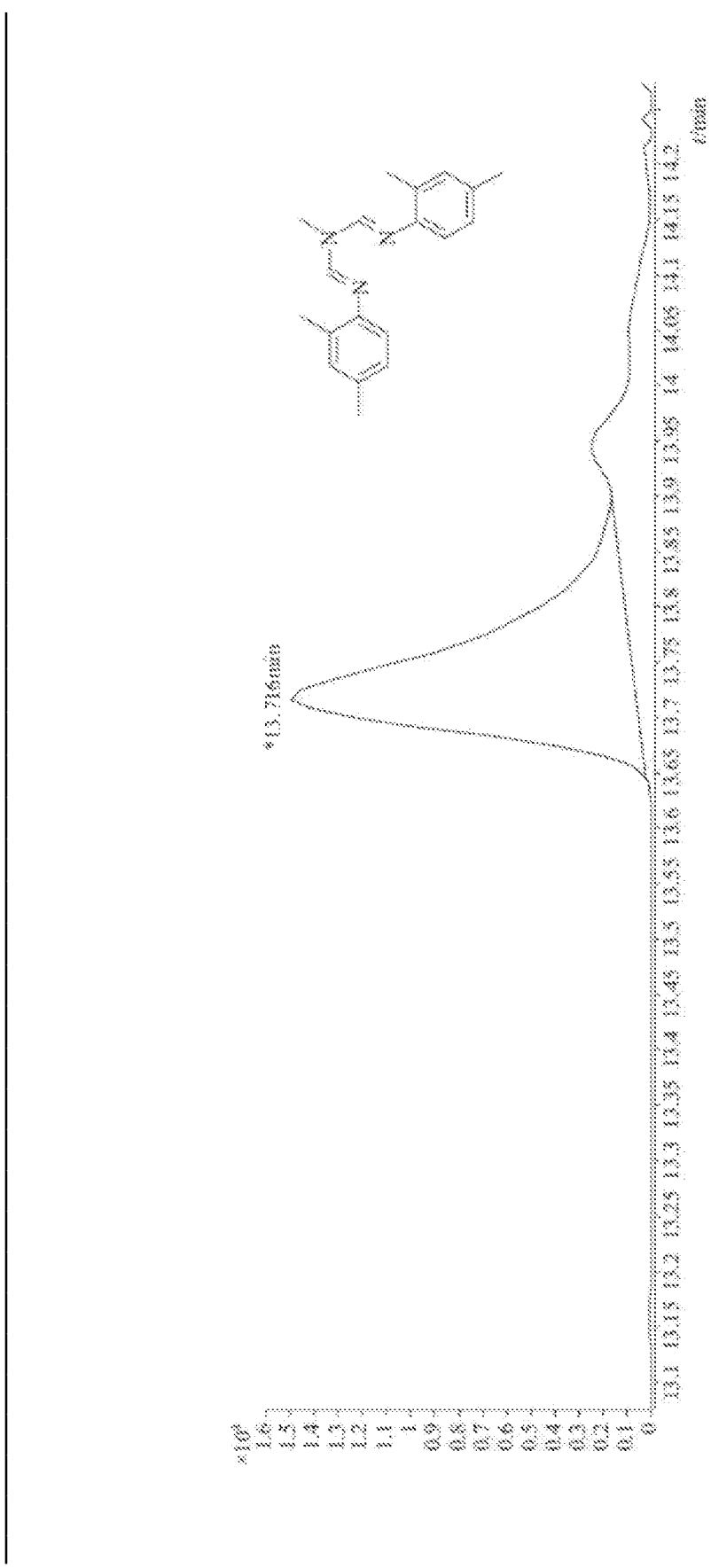
FIG. 5 is a total ion chromatogram according to an example of the present invention.
Figure 6:
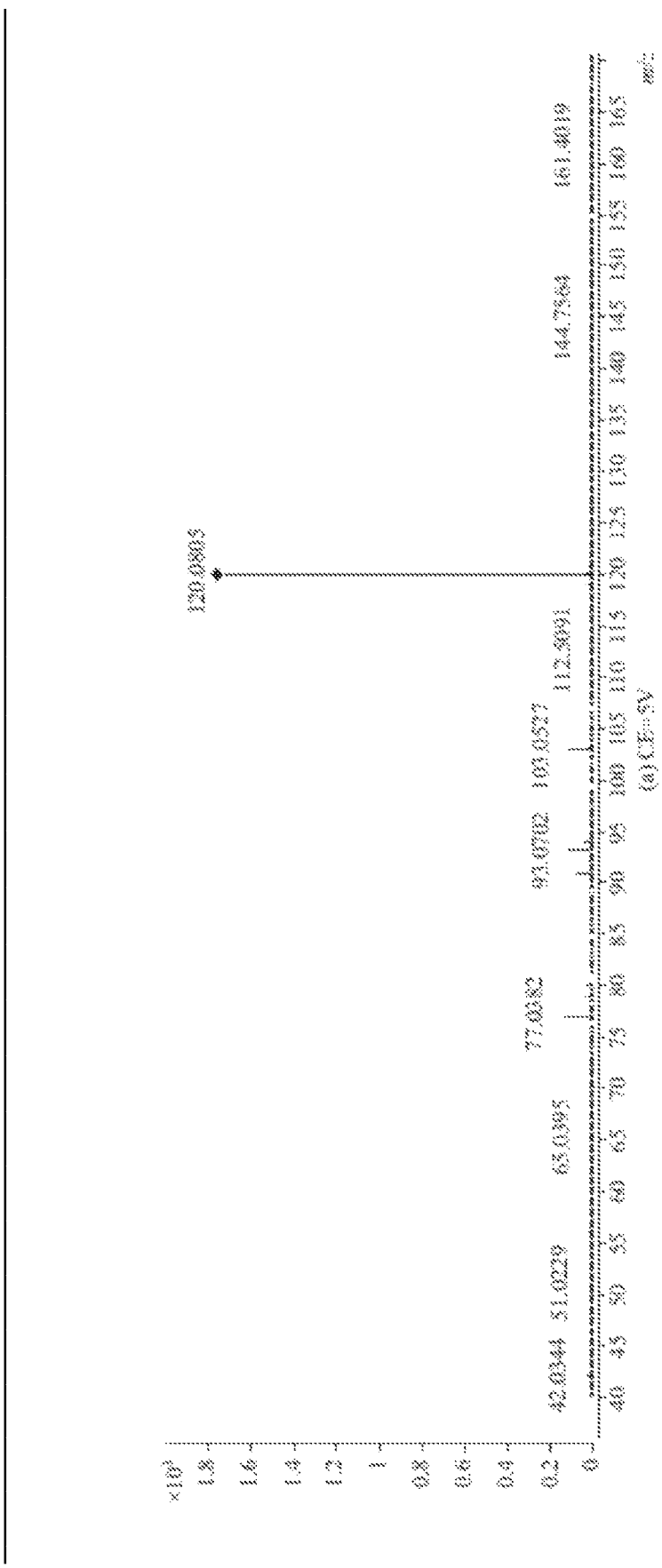
FIG. 6 is a daughter-ion mass spectrum under the corresponding collision energy according to an example of the present invention.
Figure 7:
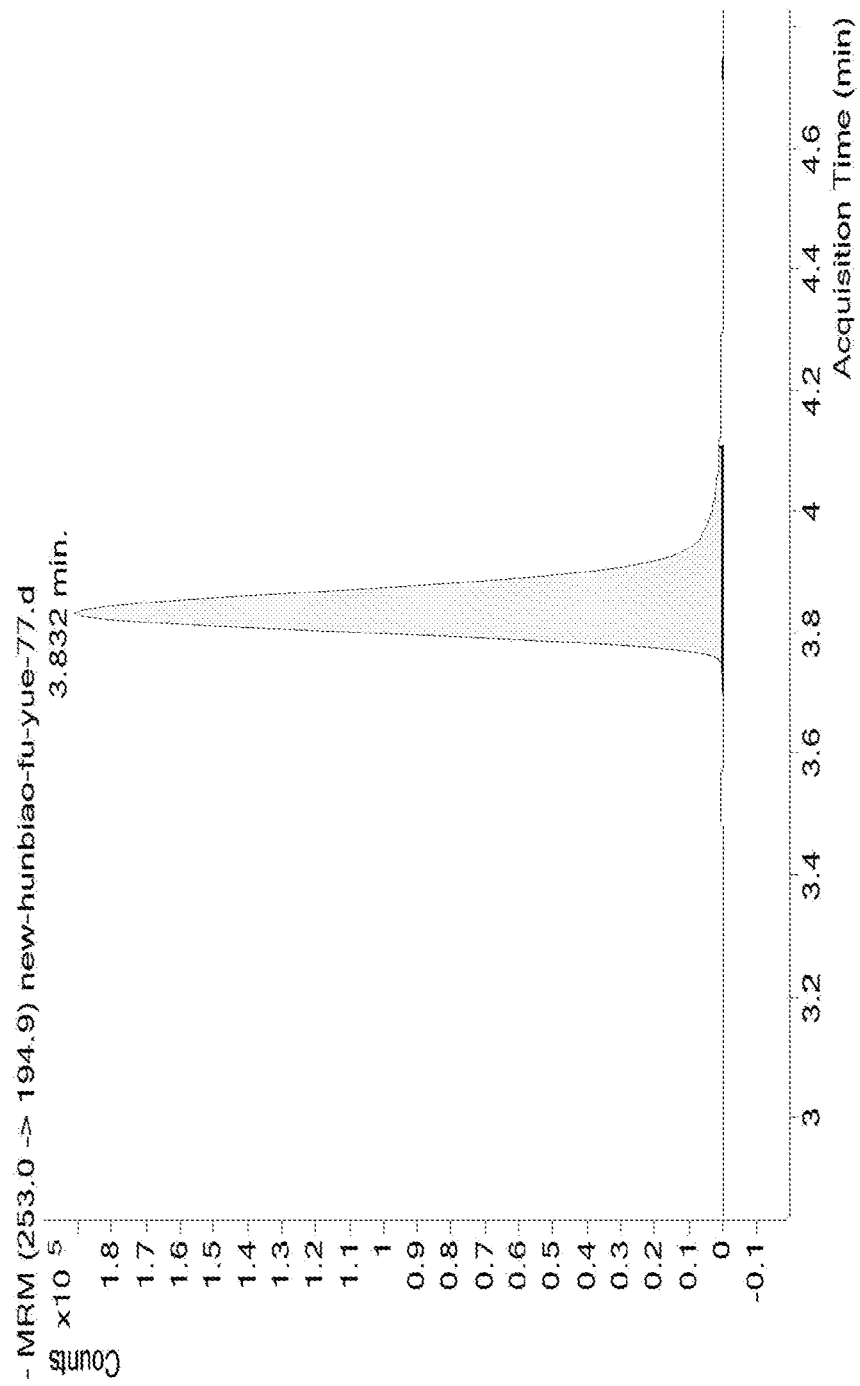
FIG. 7 is an extracted ion chromatogram according to an example of the present invention.
Figure 8:
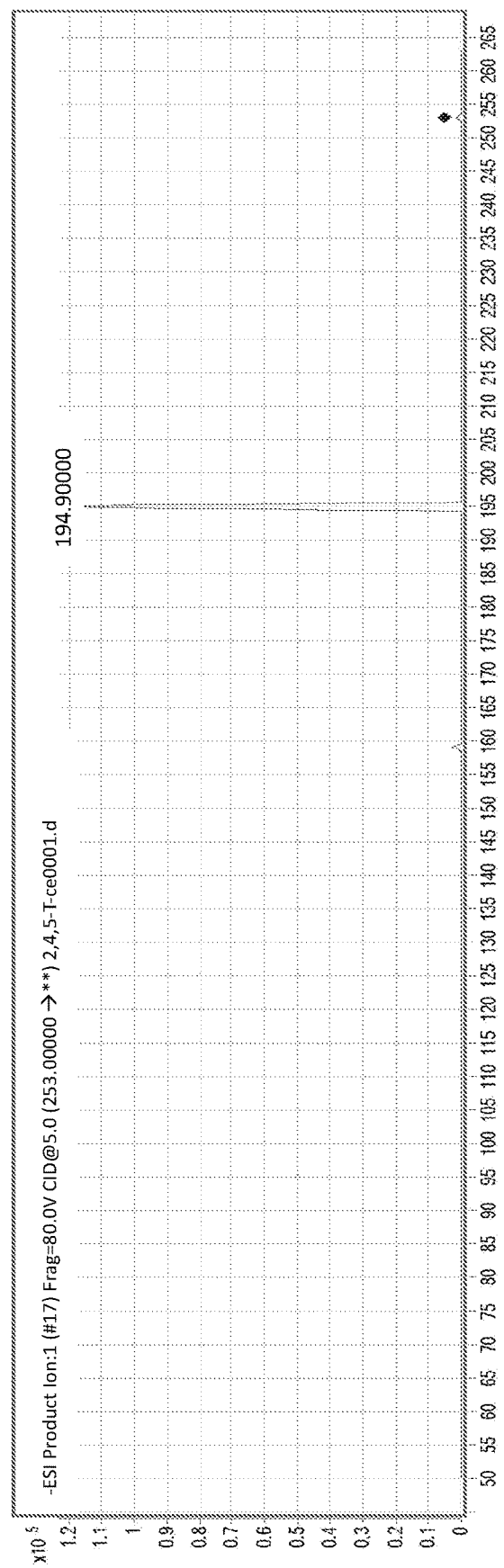
FIG. 8 is a daughter-ion mass spectrum under the corresponding collision energy according to an example of the present invention.
Figure 9:
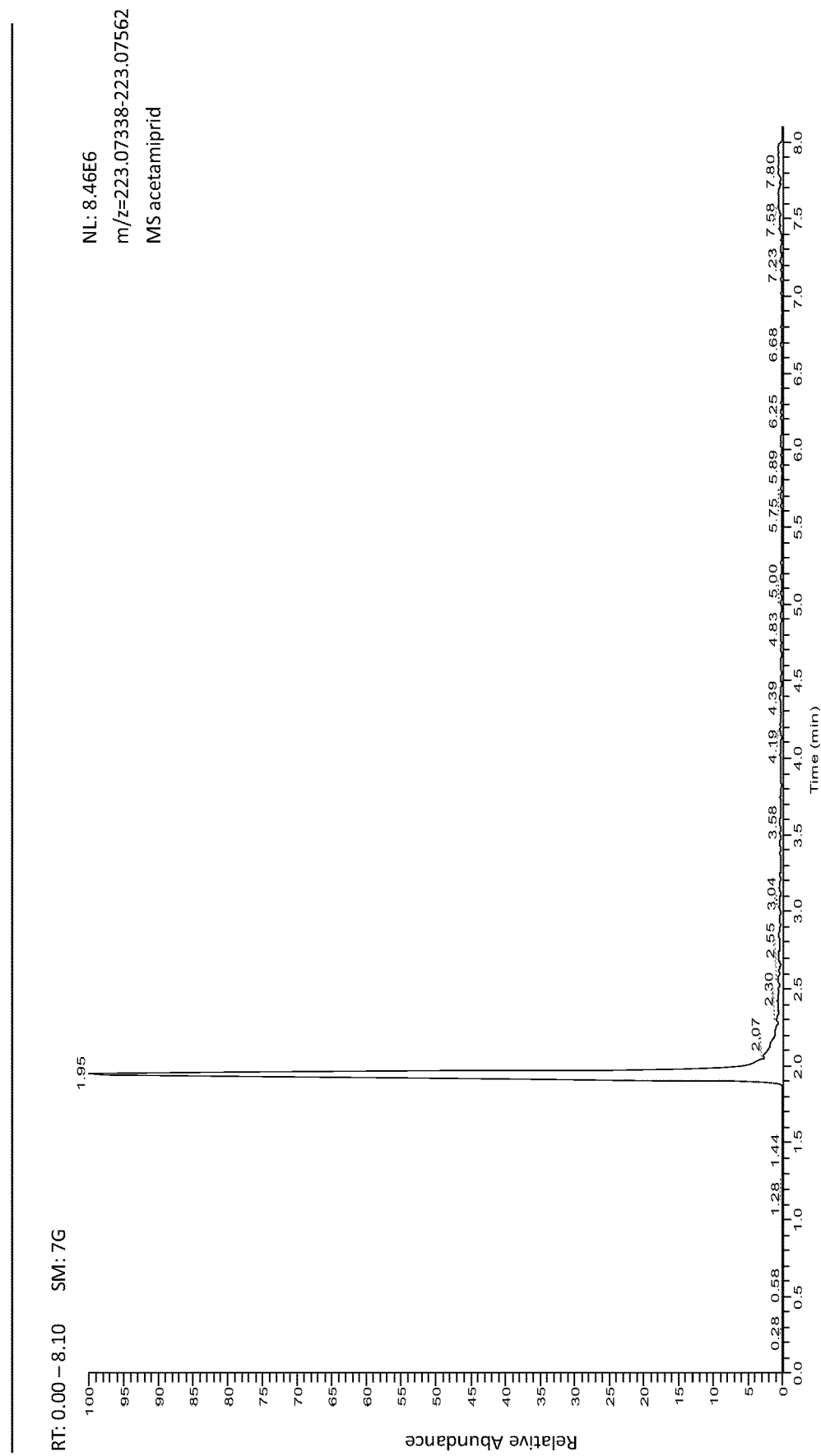
FIG. 9 is an extracted ion chromatogram of [M+H]$^+$ according to an example of the present invention.
Figure 10:
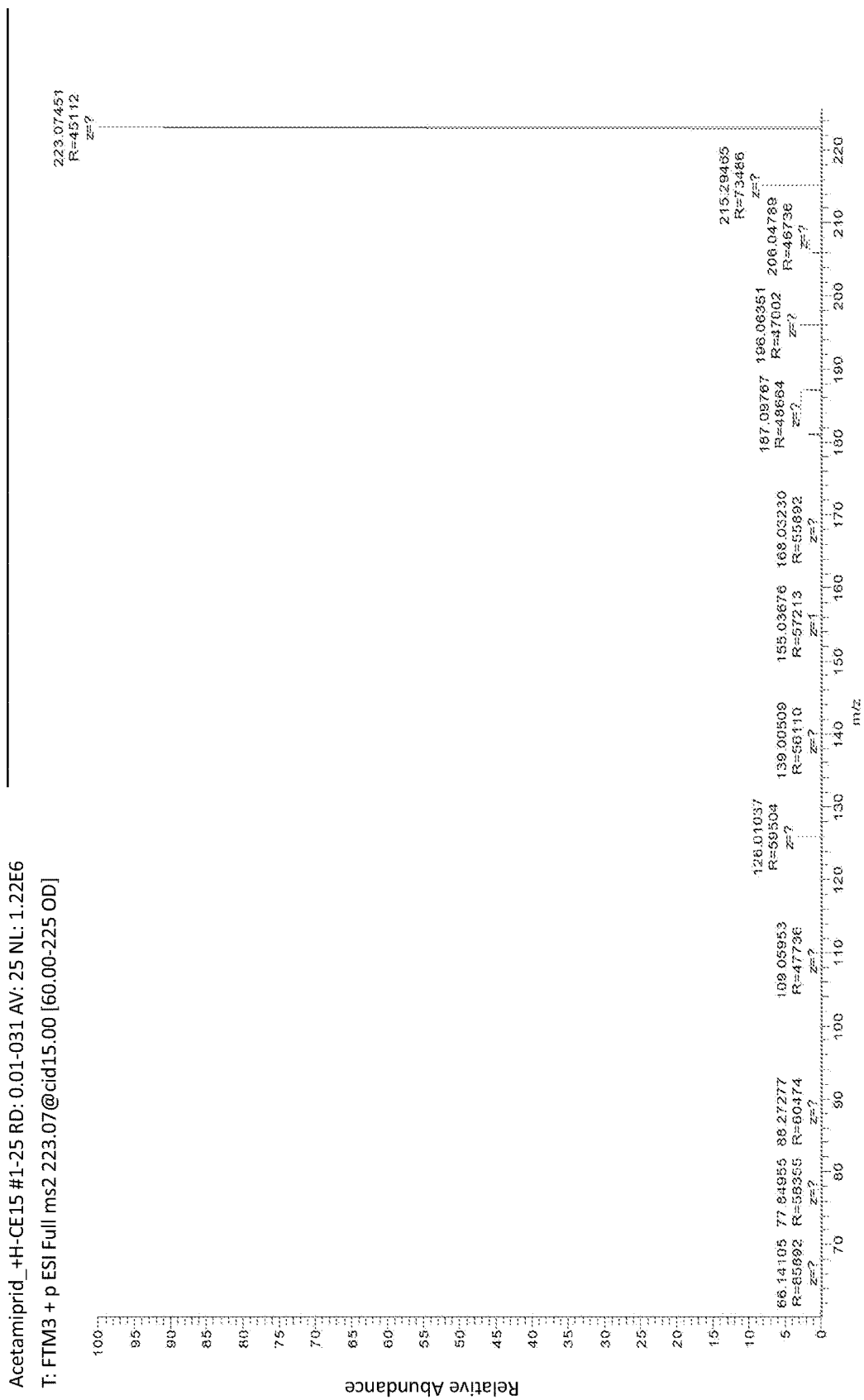
FIG. 10 is a secondary mass spectrum of [M+H]$^+$ according to an example of the present invention.
Figure 11:
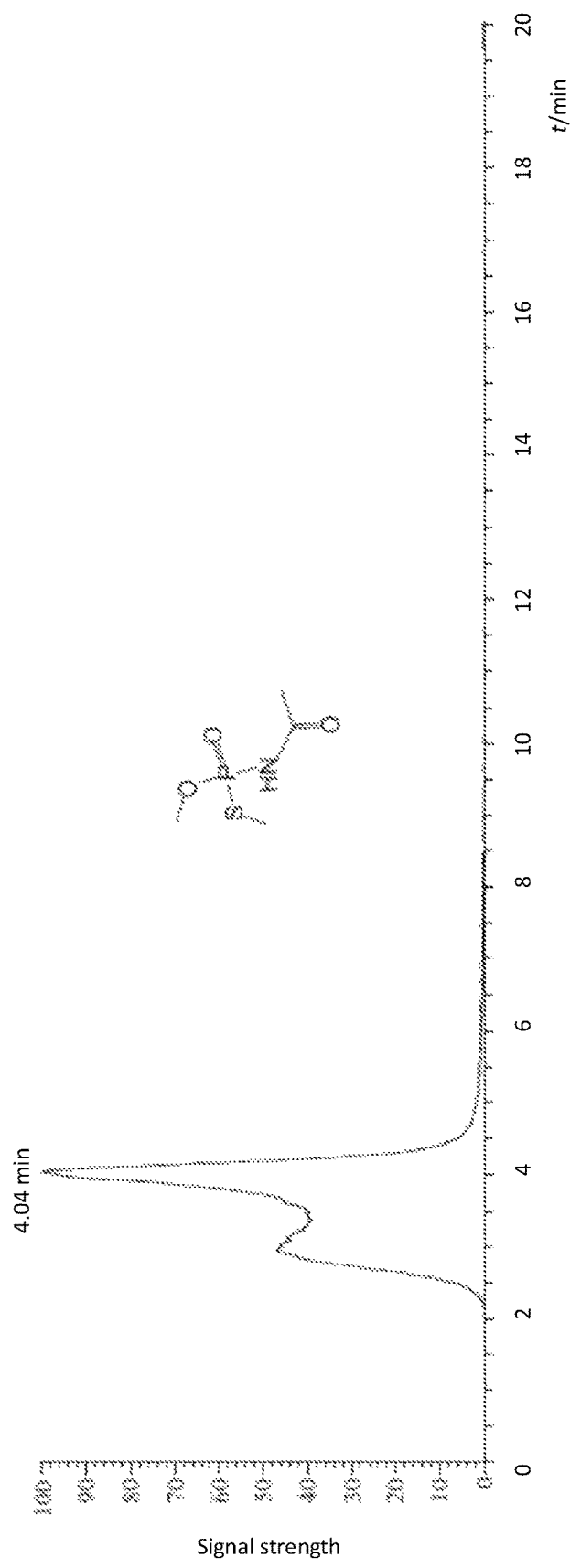
FIG. 11 is an extracted ion chromatogram according to an example of the present invention.
Figure 12:
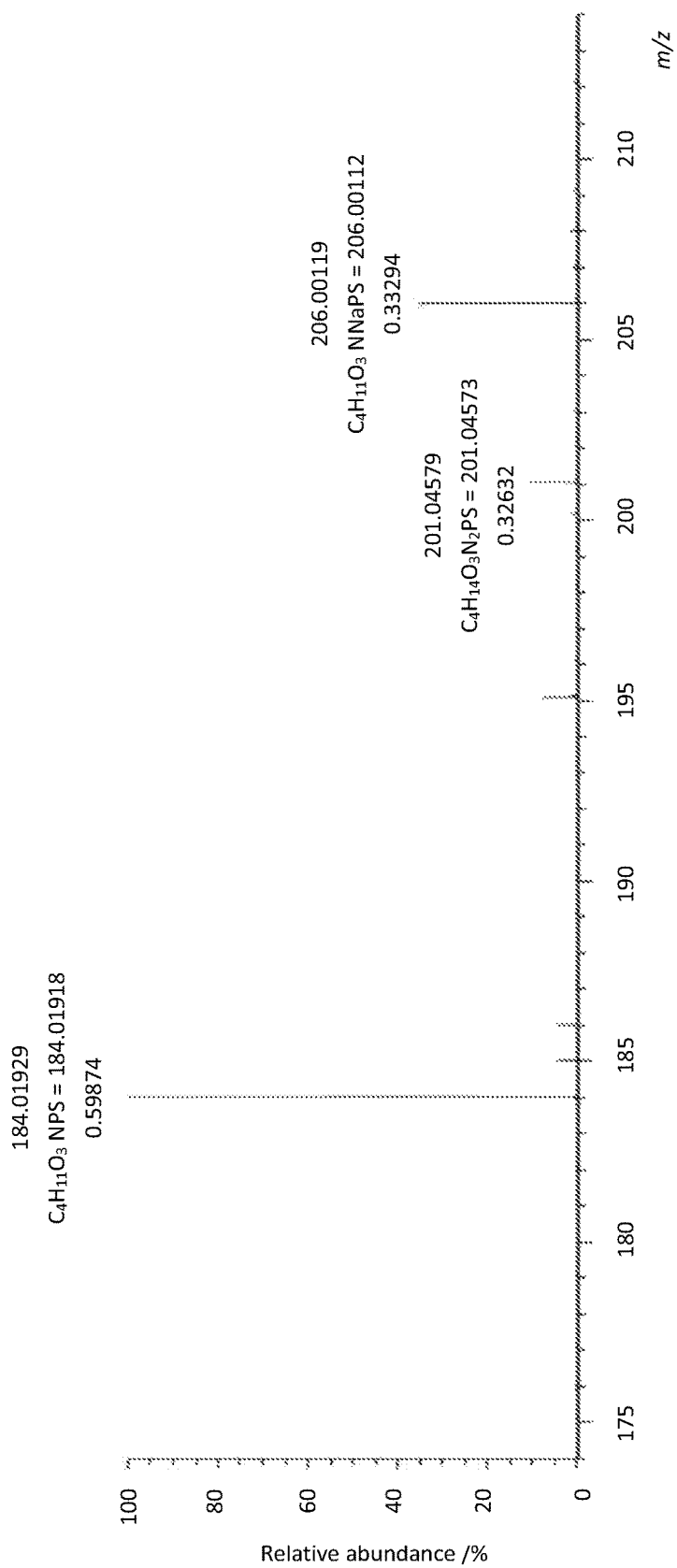
FIG. 12 is a typical primary mass spectrum of [M+H]$^+$, [M+NH$_4$]$^+$ and [M+Na]$^+$ according to an example of the present invention.

Table 1 shows the parameter chart of the layer-by-layer refinement convolutional neural network in the present invention. Wherein, the pretreated spectrum image is inputted into layer-by-layer refinement neural network, the image size of the inputted spectrum is 1×1×1626×1626, the meaning of each parameter is: one sample is selected at a time in training set to update the weight, the number of channel for input of image (binary image) is 1, the inputted image size (height×width) is 1626×1626. The first convolutional layer Conv1 uses the convolution kernel with the size of 11×11×1, which represents that after each convolution operation, the convolution kernel moves 4 pixels. The edge complement pixel p is 0, representing that the image edge is not filled. After Conv1 layer operation, the feature image is outputted, which reflects information such as the spectrum edge contour. The Relu activation function is used to map the convoluted result and control the data range. Next, the local response normalization layer LRN1 normalizes the feature data outputted from the convolutional layer Conv1, and creates a competitive mechanism for the activity of the local neurons, such that the values with larger response become relatively larger and other neurons with smaller feedback is suppressed, so as to enhance model generalization ability. After the calculation of this layer, the size of the feature image remains unchanged. Next, pooling layer Pool1 uses the kernel with the size of 3×3×64 to maximally pool the feature image outputted by the LRN1 layer and reduces calculation and parameter number by sampling. Convolutional layers Conv2-Conv5 respectively perform corresponding convolution operation for the feature image outputted from the previous layer, the convolutional kernel size is reduced layer by layer, respectively 9×9×64, 7×7×128, 5×5×256, 3×3×512, wherein 64, 128, 256 and 512 respectively correspond to the number of convolution kernels used by the convolutional layer. The more the convolutional kernel used, the higher the obtained feature dimension. After the layer-by-layer convolution operation, the lower-layer features are abstracted into higher dimensional and more refined convolution activation features. The step size and the edge complement pixel size in each convolutional layer are shown in FIG. 3. The local response normalization layer LRN2 normalizes the feature data outputted from the convolutional layer Conv2. The pooling layers Pool2-Pool5 respectively use the kernel with the size of 3×3×128, 3×3×256, 3×3×512 and 3×3×512 to maximally pool the feature image outputted by the previous layer. The fully connected layer Fc6 connects the local features outputted by the Conv5, three fully connected layers, Fc6-Fc8, filter the features which perform well in the classification task by learning all the weights during the training process, and send the features into the Softmax-loss layer. The Dropout layers, Dop6 and Drop7, are used in the calculation results of Fc6 and Fc7 respectively, and randomly disable partial nodes of the hidden layer to speed up the training speed and prevent overfitting. The Softmax-loss layer is like a classifier, and calculates the value of loss function in the training process, the stochastic gradient descent algorithm is used to update the weight and the initial learning rate is set as 0.0001. By minimizing the loss function, the classification effect is gradually improved, and a layer-by-layer refinement convolutional neural network classification model having better classification effect is obtained. The person skilled in the art should understand that the parameters mentioned above, such as the spectrum size, the convolutional kernel size etc., are exemplary, and can be changed adaptively according to the actual needs of the system.

TABLE 1

| Layer type | Input Image size | Output Image size | Kernel size k, Step size s, Edge complement pixel p |
|---|---|---|---|
| Conv1 | 11 × 1626 × 1626 | 1 × 64 × 404 × 404 | 11 × 11 × 1, 4, 0 |
| LRN1 | 1 × 64 × 404 × 404 | 1 × 64 × 404 × 404 | |
| Pool1 | 1 × 64 × 404 × 404 | 1 × 64 × 202 × 202 | 3 × 3 × 64 |
| Conv2 | 1 × 64 × 202 × 202 | 1 × 128 × 198 × 198 | 9 × 9 × 64, 1, 2 |
| LRN2 | 1 × 128 × 198 × 198 | 1 × 128 × 198 × 198 | |
| Pool2 | 1 × 128 × 198 × 198 | 1 × 128 × 99 × 99 | 3 × 3 × 128 |
| Conv3 | 1 × 128 × 99 × 99 | 1 × 256 × 95 × 95 | 7 × 7 × 128, 1, 1 |
| Pool3 | 1 × 256 × 95 × 95 | 1 × 256 × 47 × 47 | 3 × 3 × 256 |
| Conv4 | 1 × 256 × 47 × 47 | 1 × 512 × 45 × 45 | 5 × 5 × 256, 1, 1 |
| Pool4 | 1 × 512 × 45 × 45 | 1 × 512 × 22 × 22 | 3 × 3 × 512 |
| Conv5 | 1 × 512 × 22 × 22 | 1 × 512 × 22 × 22 | 3 × 3 × 512, 1, 1 |
| Pool5 | 1 × 512 × 22 × 22 | 1 × 512 × 11 × 11 | 3 × 3 × 512 |
| Fc6 | 1 × 512 × 11 × 11 | 1 × 512 | |
| Drop6 | 1 × 512 | 1 × 512 | |
| Fc7 | 1 × 512 | 1 × 512 | |
| Drop7 | 1 × 512 | 1 × 512 | |
| Fc8 | 1 × 512 | 1 × 3465 | |
| Softmax-loss | 1 × 3465 | 1 | |

The examples of the system and method described above are only exemplary, wherein the units as separate components may or may not be physically separated, and the components displayed as the units may or may not be physical units, that is, they can be located in one place or distributed in multiple network units. Partial or all unit modules can be selected to achieve the purpose of the solution of the example according to the actual needs. The person skilled in the art can understand and implement without creative work.

Through the description of the above embodiments, the person skilled in the art can clearly understand that the embodiment can be implemented in foreground or background. The described foreground includes the spectrum comparison and identification software, the spectrum species identification method; the background only includes training for identification of the spectrum model and the method of constructing mass spectrum identification. Based on the above understanding, the essence or the part making contribution to the prior art of above described technical solutions may be embodied in the form of software product. The computer software product can be stored in a computer readable storage medium such as ROM/RAM, diskette, or optical disk etc, and includes a number of commands for causing a computer device (which may be a personal computer, server, or network device, etc.) to execute the methods described in each example or some part of the example. If the system wants to identify more spectrums, it is necessary to obtain more types and amounts of spectrums for identification and modeling.

Finally, it should be noted that the above examples are only used to illustrate the technical solution of the present invention, and are not intended to limit the present invention; although the present invention has been described in detail with reference to the previous examples, the person skilled in the art should understand that the technical solution described in the above examples can be amended, or some of the technical feature can be equivalently replaced. Those amendment and replacement will not make the essence of the technical solution deviate from the spirit and scope of the technical solutions of the examples of the present invention.

The detailed descriptions set forth above are merely illustrative of the possible embodiments of the present invention, and are not intended to limit the scope of the present invention. Equivalent embodiments or amendments that do not depart from the spirit of the invention are intended to be included within the protection scope of the present invention.

The invention claimed is:

1. A cloud-platform based identification system of seven types of mass spectrums for pesticides and chemical pollutants commonly used in the world, including a cloud server platform end and a user platform end, wherein the cloud server platform end includes:
a spectrum acquisition unit, which is used to acquire mass spectrum;
a spectrum parameter acquisition unit, which is used to acquire the experiment environment, experiment condition, and experiment parameter data corresponding to the mass spectrum;
a spectrum device acquisition unit, which is used to acquire information of the spectrum detection device corresponding to the mass spectrum;
a spectrum pretreatment unit, which is used to longitudinally splice and pretreat the acquired mass spectrum and extract the spectrum features; and
a pesticide species classification model unit, which is used to train the extracted spectrum features, spectrum detection device information and experimental parameter data by neural network model and to obtain the classification model which can identify the species and/or names of pesticides and chemical pollutants;
and wherein the user platform end includes:
a spectrum data uploading unit, which is used to upload the mass spectrum, spectrum description data and experiment parameter data to the system for detection;
a spectrum pretreatment unit, which is used to longitudinally splice and pretreat the mass spectrum to be detected and extract the mass spectrum features; and
a spectrum identification unit, which is used to input the extracted spectrum features, spectrum description data and experiment parameter data to the pesticide species classification model, to identify the species and/or names of the corresponding pesticides and chemical pollutants.

2. The cloud-platform based identification system of seven types of mass spectrums for pesticides and chemical pollutants commonly used in the world according to claim 1, wherein,
the cloud platform server end further includes: a mass spectrum classification model unit, which is used to acquire the change value of fitting angle at the pixel point where the highest peak inside the mass spectrum is located and construct mass spectrum classification model; and
the user platform end further includes: a mass spectrum species identification unit, which is used to acquire the result of mass spectrum classification according to the change value of fitting angle at the pixel point where the highest peak inside the mass spectrum is located, which is calculated by the mass spectrum classification model unit.

3. The cloud-platform based identification system of seven types of mass spectrums for pesticides and chemical pollutants commonly used in the world according to claim 2, wherein the cloud platform server end includes a mass spectrum information base, and the user platform end further includes a user retrieval unit; the mass spectrum species identification unit utilizes the user retrieval unit to screen the mass spectrum data which may be similar to the species of mass spectrum to be detected from said mass spectrum information base, according to the mass spectrum description data, experiment parameters and number of mass spectrums before inputting the mass spectrum to be detected into the mass spectrum classification model; the Fc7 layer features are extracted from the mass spectrum to be detected, and the cosine similarity between the Fc7 layer feature and the Fc7 layer features of all pretreated mass spectrum selected from the base to identify the mass spectrum with the highest degree of similarity to the current mass spectrum to be detected and determine whether the similarity is higher than 50%; if the similarity is higher than 50%, the mass spectrum inputted by the user is identified successfully.

4. The cloud-platform based identification system of seven types of mass spectrums for pesticides and Chemical pollutants commonly used in the world according to claim 1, wherein the neural network model used in the pesticide species classification model unit is a layer-by-layer refinement convolutional neural network model, the design or usage method thereof is as following:
after pretreatment, mass spectrum is inputted to the layer-by-layer refinement convolutional neural network model for training in the size of 1×1×1626×1626, the meaning of each parameter is: one sample is selected at a time in training set to update the weight, the number of channel for input of image is 1, the inputted image size is 1626×1626;
the first convolutional layer Conv1 uses the convolution kernel with the size of 11×11×1, which represents that after each convolution operation, the convolution kernel moves 4 pixels; the edge complement pixel p is 0, representing that the image edge is not filled; after Conv1 layer operation, the feature image is outputted, which reflects information such as the spectrum edge contour; the Relu activation function is used to map the convoluted result and control the data range; next, the local response normalization layer LRN1 normalizes the feature data outputted from the convolutional layer Conv1, and creates a competitive mechanism for the activity of the local neurons, such that the values with larger response become relatively larger and other neurons with smaller feedback is suppressed, so as to enhance model generalization ability; after the calculation of this layer, the size of the feature image remains unchanged; next, pooling layer Pool1 uses the kernel with the size of 3×3×64 to maximally pool the feature image outputted by the LRN1 layer and reduces calculation and parameter number by sampling;
convolutional layers Conv2-Conv5 respectively perform corresponding convolution operation for the feature image outputted from the previous layer, the convolutional kernel size is reduced layer by layer, respectively 9×9×64, 7×7×128, 5×5×256, 3×3×512, wherein 64, 128, 256 and 512 respectively correspond to the number of convolution kernels used by the convolutional layer; after the layer-by-layer convolution operation, the lower-layer features are abstracted into higher dimensional and more refined convolution activation features; the local response normalization layer LRN2 normalizes the feature data outputted from the convolutional layer Conv2, The pooling layers Pool2-Pool5 respectively use the kernel with the size of 3×3×128, 3×3×256, 3×3×512 and 3×3×512 to maximally pool the feature image outputted by the previous layer;

the fully connected layer Fc6 connects the local features outputted by the Conv5, three fully connected layers, Fc6-Fc8, filter the features which perform well in the classification task by learning all the weights during the training process, and send the features into the Softmax-loss layer; the Dropout layers, Drop6 and Drop7, are used in the calculation results of Fc6 and Fc7 respectively, and randomly disable partial nodes of the hidden layer to speed up the training speed and prevent overfitting; the Softmax-loss layer calculates the value of loss function;

in the training process, the stochastic gradient descent algorithm is used to update the weight and the initial learning rate is set as 0.0001; and by minimizing the loss function, the classification effect is gradually improved, and a layer-by-layer refinement convolutional neural network classification model having better classification effect is obtained.

5. The cloud-platform based identification system of seven types of mass spectrums for pesticides and chemical pollutants commonly used in the world according to claim 2, wherein the mass spectrum classification model unit classifies, according to the change value of angle at the pixel point where the highest peak inside the mass spectrum is located: the change value of fitting angle of the ion chromatogram in liquid chromatography-tandem mass spectrum is in the range of $x_{11}$-$x_{12}$, and the change value of fitting angle of ion mass spectrum under 4 collision energies is in the range of $x_{13}$-$x_{14}$; the change value of fitting angle of the ion chromatogram in liquid chromatography-quadrupole-time of flight mass spectrometry is in the range of $x_{21}$-$x_{22}$, and the value of fitting angle of ion mass spectrum under 4 collision energies is $x_{23}$; the change value of fitting angle of the ion chromatogram in linear ion trap-electric field cyclotron resonance orbit trap combined mass spectrum, is in the range of $x_{31}$-$x_{32}$, the value of fitting angle of full scan mass spectrum under ionization mode is $x_{33}$; the change value of fitting angle of the primary mass spectrum in gas chromatography-tandem mass spectrum is $x_{41}$, the value of fitting angle of ion mass spectrum under 4 collision energies is $x_{43}$; the change value of fitting angle of the ion chromatogram in liquid chromatography-quadrupole-electrostatic field orbit trap mass spectrometry is $x_{51}$, the value of fitting angle of fragment ion mass spectrum is $x_{53}$; the value of fitting angle of the mass spectrum in gas chromatography-quadrupole-time of flight mass spectrum is $x_{61}$; the change value of fitting angle of the total ion chromatogram in gas chromatography-quadrupole-electrostatic field orbit trap mass spectrometry is iii the range of $x_{71}$-$x_{72}$, the value of fitting angle of full scan mass spectrum under ionization mode is $x_{73}$, wherein value range of $x_{11}$-$x_{73}$ is 0°-40°.

6. The cloud-platform based identification system of seven types of mass spectrums for pesticides and chemical pollutants commonly used in the world according to claim 2, wherein the change value of angle at the pixel point, where the highest peak inside the mass spectrum is located, is calculated according to the gradient vector; around a straight line or a curve, the gradient vector is perpendicular to the straight line or the curve, the angle could be calculated by the orientation change of gradient vector; the gradient vector at a point on the curve is the vertical line of the curve segment passing through the point; a short line segment near the point replaces the curve segment, and the vertical line of the line segment is calculated as the gradient vector; the line segment near the point is determined by the neighborhood chain length, the orientation of the gradient vector is its angle size.

7. The cloud-platform based identification system of seven types of mass spectrums for pesticides and chemical pollutants commonly used in the world according to claim 6, wherein the calculation method of the fitting angle change value at the pixel point of the highest peak in the mass spectrum is as following: $P_n=\{p_1, \ldots, p_n\}$ is the ordered points set on a curve or a straight line, $L_n=\{l_1, \ldots, l_n\}$ is a short line segment near the ordered points on a curve or a straight line, $l_i (i=1, \ldots, n)$ represents the line segment with point pi as the center and having a neighborhood chain length of m (i.e., connecting points $p_{i-m}$ and $p_{i+m}$), $S_n=\{s_1, \ldots, s_n\}$ represents the set of slopes of the vertical line of line segment $l_i$, $A_n=\{a_1, \ldots, a_n\}$ represents the set of angle of the vertical line of $l_i$ near point $p_i$, $a_i$ is in the range of [0, 360°];

the slope of the line segment $l_i$ near the point $p_i(x_i, y_i)$ (connecting the point $p_{i-m}(x_{i-m}, y_{i-m})$ and the point $p_{i+m}(x_{i+m}, y_{i+m})$) is:

$$g_i = (y_{i+m} - y_{i-m})/(x_{i+m} - x_{i-m});$$

the slope of vertical line of line segment $l_i$ is $(-1/g_i)$, i.e.:

$$s_i = (x_{i+m} - x_{i-m})/(y_{i+m} - y_{i-m})$$

the calculation method of $a_i$: when there is no slope, $a_i = \pi/2$; when the slope is 0, $a_i = \pi$; when the slope is greater than 0, $a_i = \arctan k_i$; when the slope is smaller than 0, $a_i = \pi + \arctan k_i$.

8. The cloud-platform based identification system of seven types of mass spectrums for pesticides and chemical pollutants commonly used in the world according to claim 1, wherein the spectrums include one or more of the following: liquid chromatography-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

9. The cloud-platform based identification system of seven types of mass spectrums for pesticides and chemical pollutants commonly used in the world according to claim 8, wherein the mass spectrum could be extracted ion chromatogram.

10. A cloud-platform based identification system of seven types of mass spectrums for pesticides and chemical pollutants commonly used in the world, wherein
at the cloud server platform end:
to acquire mass spectrum and to acquire the experiment environment, experiment condition and experiment parameter data corresponding to the mass spectrum;
to acquire the detection device information corresponding to the mass spectrum;
to longitudinally splice and pretreat the acquired mass spectrum and to extract the features thereof;
to acquire a change value of fitting angle at a pixel point where the highest peak inside the mass spectrum is located, and to construct a mass spectrum classification model;
to use the neural network model to train the extracted mass spectrum feature, spectrum detection device information and experiment parameter data, and to obtain a pesticide species classification model which can identify the species and/or name of pesticides and chemical pollutants; and wherein at the user platform end:
to upload the mass spectrum to be detected, mass spectrum description data and experimental parameter data to the cloud server platform end;
to longitudinally splice and pretreat the mass spectrum to be detected, and to extract the features of the mass spectrum;
to receive the result of mass spectrum classification from the cloud server platform end;
to upload the extracted spectrum features, mass spectrum description data and experiment parameter data into the pesticide species classification model at the cloud server platform end and to receive the identified species and/or name of corresponding pesticides and chemical pollutants.

11. The cloud-platform based identification system of seven types of mass spectrums for pesticides and chemical pollutants commonly used in the world according to claim 10, wherein the neural network model is a layer-by-layer refinement convolutional neural network model, the design or usage method thereof is as following:
after pretreatment, spectrum is inputted to the layer-by-layer refinement convolutional neural network model for training in the size of 1×1×1626×1626, the meaning of each parameter is: one sample is selected at a time in training set to update the weight, the number of channel for input of image is 1, the inputted image size is 1626×1626;
the first convolutional layer Conv1 uses the convolution kernel with the size of 11×11×1, which represents that after each convolution operation, the convolution kernel moves 4 pixels; the edge complement pixel p is 0, representing that the image edge is not filled; after Conv1 layer operation, the feature image is outputted, which reflects information such as the spectrum edge contour; the Relu activation function is used to map the convoluted result and control the data range; next, the local response normalization layer LRN1 normalizes the feature data outputted from the convolutional layer Conv1, and creates a competitive mechanism for the activity of the local neurons, such that the values with larger response become relatively larger and other neurons with smaller feedback is suppressed, so as to enhance model generalization ability; after the calculation of this layer, the size of the feature image remains unchanged; next, pooling layer Pool1 uses the kernel with the size of 3×3×64 to maximally pool the feature image outputted by the LRN1 layer and reduces calculation and parameter number by sampling;
convolutional layers Conv2-Conv5 respectively perform corresponding convolution operation for the feature image outputted from the previous layer, the convolutional kernel size is reduced layer by layer, respectively 9×9×64, 7×7×128, 5×5×256, 3×3×512, wherein 64, 128, 256 and 512 respectively correspond to the number of convolution kernels used by the convolutional layer; after the layer-by-layer convolution operation, the lower-layer features are abstracted into higher dimensional and more refined convolution activation features; the local response normalization layer LRN2 normalizes the feature data outputted from the convolutional layer Conv2, The pooling layers Pool2-Pool5 respectively use the kernel with the size of 3×3×128, 3×3×256, 3×3×512 and 3×3×512 to maximally pool the feature image outputted by the previous layer;
the fully connected layer Fc6 connects the local features outputted by the Conv5, three fully connected layers, Fc6-Fc8, filter the features which perform well in the classification task by learning all the weights during the training process, and send the features into the Softmax-loss layer; the Dropout layers, Drop6 and Drop7, are used in the calculation results of Fc6 and Fc7 respectively, and randomly disable partial nodes of the hidden layer to speed up the training speed and prevent overfitting; the Softmax-loss layer calculates the value of loss function;
in the training process, the stochastic gradient descent algorithm is used to update the weight and the initial learning rate is set as 0.0001; and by minimizing the loss function, the classification effect is gradually improved, and a layer-by-layer refinement convolutional neural network classification model having better classification effect is obtained.

12. The cloud-platform based identification system of seven types of mass spectrums for pesticides and chemical pollutants commonly used in the world according to claim 10, wherein the mass spectrum classification model unit classifies, according to the change value of angle at the pixel point where the highest peak inside the mass spectrum is located: the change value of fitting angle of the ion chromatogram in liquid chromatography-tandem mass spectrum is in the range of $x_{11}$-$x_{12}$, and the change value of fitting angle of ion mass spectrum wider 4 collision energies is in the range of $x_{13}$-$x_{14}$; the change value of fitting angle of the ion chromatogram in liquid chromatography-quadrupole-time of flight mass spectrometry is in the range of $x_{21}$-$x_{22}$, and the value of fitting angle of ion mass spectrum under 4 collision energies is $x_{23}$; the change value of fitting angle of the ion chromatogram in linear ion trap-electric field cyclotron resonance orbit trap combined mass spectrum, is in the range of $x_{31}$-$x_{32}$, the value of fitting angle of full scan mass spectrum under ionization mode is $x_{33}$; the change value of fitting angle of the primary mass spectrum in gas chromatography-tandem mass spectrum is $x_{41}$, the value of fitting angle of ion mass spectrum under 4 collision energies is $x_{43}$; the change value of fitting angle of the ion chromatogram in liquid chromatography-quadrupole-electrostatic field orbit trap mass spectrometry is $x_{51}$, the value of fitting angle of fragment ion mass spectrum is $x_{53}$; the value of fitting angle of the mass spectrum in gas chromatography-quadrupole-time of flight mass spectrum is $x_{61}$; the change value of fitting angle of the total ion chromatogram in gas chromatography-quadrupole-electrostatic field orbit trap mass spectrometry is in the range of $x_{71}$-$x_{72}$, the value of fitting angle of full scan mass spectrum under ionization mode is $x_{73}$, wherein value range of $x_{11}$-$x_{73}$ is 0°-40°.

13. The cloud-platform based identification system of seven types of mass spectrums for pesticides and chemical pollutants commonly used in the world according to claim 10, wherein the change value of angle at the pixel point, where the highest peak inside the mass spectrum is located, is calculated according to the gradient vector; around a straight line or a curve, the gradient vector is perpendicular to the straight line or the curve, the angle could be calculated by the orientation change of gradient vector; the gradient vector at a point on the curve is the vertical line of the curve segment passing through the point; a short line segment near the point replaces the curve segment, and the vertical line of the line segment is calculated as the gradient vector; the line segment near the point is determined by the neighborhood chain length, the orientation of the gradient vector is its angle size;

the calculation method is as following:

$P_n = \{p_1, \ldots, p_n\}$ is the ordered points set on a curve or a straight line, $L_n = \{l_1, \ldots, l_n\}$ is a short line segment near the ordered points on a curve or a straight line, $l_i$ ($i=1, \ldots, n$) represents the line segment with point pi as the center and having a neighborhood chain length of m (i.e., connecting points $p_{i-m}$ and $p_{i+m}$), $S_n = \{s_1, \ldots, s_n\}$ represents the set of slopes of the vertical line of line segment $l_i$, $A_n = \{a_1, \ldots, a_n\}$ represents the set of angle of the vertical line of $l_i$ near point $p_i$, $a_i$ is in the range of [0, 360°];

the slope of the line segment $l_i$ near the point $p_i(x_i, y_i)$ (connecting the point $p_{i-m}(x_{i-m}, y_{i-m})$ and the point $p_{i+m}(x_{i+m}, y_{i+m})$) is:

$$g_i = (y_{i+m} - y_{i-m})/(x_{i+m} - x_{i-m});$$

the slope of vertical line of line segment $l_i$ is $(-1/g_i)$, i.e.:

$$s_i = (x_{i+m} - x_{i-m})/(y_{i+m} - y_{i-m});$$

the calculation method of $a_i$: when there is no slope, $a_i = \pi/2$; when the slope is greater than 0, $a_i = \arctan k_i$; when the slope is smaller than 0, $a_i = \pi + \arctan k_i$.

14. The cloud-platform based identification system of seven types of mass spectrums for pesticides and chemical pollutants commonly used in the world according to claim 10, wherein the method for the user to receive the mass spectrum classification result returned from the cloud server platform end includes: according to the mass spectrum description data, experiment parameters and mass spectrum mount, the classification result is directly screened and obtained from the mass spectrum information base of the cloud platform server end;

the Fc7 layer features are extracted from the mass spectrum to be detected, and the cosine similarity between this Fc7 layer feature and the Fc7 layer features of all pretreated mass spectrum selected from the base to find the mass spectrum with the highest degree of similarity to the current mass spectrum to be detected and determine whether the similarity is higher than 50%; if the similarity is higher than 50%, the mass spectrum inputted by the user is identified successfully.

15. The cloud-platform based identification system of seven types of mass spectrums for pesticides and chemical pollutants commonly used in the world according to claim 2, wherein the spectrums include one or more of the following: liquid chromatography-tandem mass spectrum, gas chromatography-tandem mass spectrum, liquid chromotography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

16. The cloud-platform based identification system of seven types of mass spectrums for pesticides and chemical pollutants commonly used in the world according to claim 3, wherein the spectrums include one or more of the following: liquid chromatography-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

17. The cloud-platform based identification system of seven types of mass spectrums for pesticides and chemical pollutants commonly used in the world according to claim 4, wherein the spectrums include one or more of the following: liquid chromatography-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

18. The cloud-platform based identification system of seven types of mass spectrums for pesticides and chemical pollutants commonly used in the world according to claim 5, wherein the spectrums include one or more of the following: liquid chromatography-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

19. The cloud-platform based identification system of seven types of mass spectrums for pesticides and chemical pollutants commonly used in the world according to claim 6, wherein the spectrums include one or more of the following: liquid chromatography-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

20. The cloud-platform based identification system of seven types of mass spectrums for pesticides and chemical pollutants commonly used in the world according to claim 7, wherein the spectrums include one or more of the following: liquid chromatography-tandem mass spectrum, gas chromatography-tandem mass spectrum, liquid chromatography-quadrupole-time of flight mass spectrum, gas chromatography-quadrupole-time of flight mass spectrum, linear ion trap-electric field cyclotron resonance orbit trap combined mass spectrum, liquid chromatography-quadrupole-electrostatic field orbit trap mass spectrum and gas chromatography-quadrupole-electrostatic field orbit trap mass spectrum.

* * * * *